Feb. 22, 1966 C. H. FISCHER Plant Pat. 2,605
GLADIOLUS PLANT
Filed Oct. 14, 1964
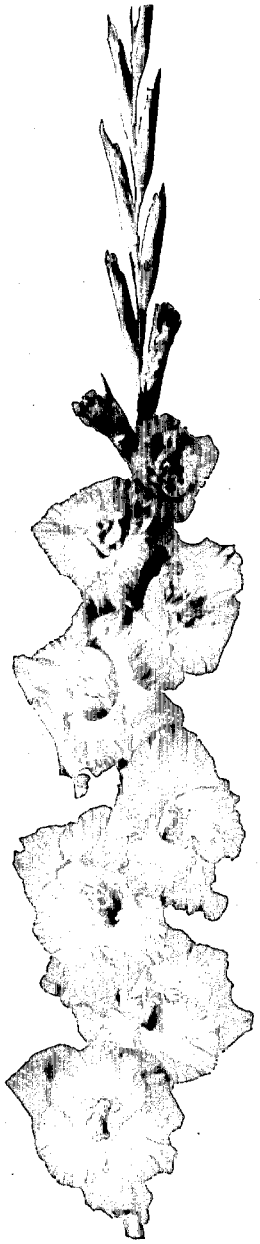
INVENTOR
Carl H. Fischer
By Lamont Johnston
ATTORNEY United States Patent Office Plant Pat. 2,605
Patented Feb. 22, 1966

2,605
GLADIOLUS PLANT

Carl H. Fischer, St. Charles, Minn., assignor to Selected Glads, Inc., New Albany, Ind., a corporation of Tennessee Filed Oct. 14, 1964, Ser. No. 403,966
1 Claim. (Cl. Plt.—85)

My present invention relates to a new and improved variety of gladiolus and is notable for its extreme ruffling, unusual color and rugged vigor. I have identified this new variety as seedling #1485–58 in my breeding work.

To the best of my knowledge, this variety is the result of a cross between an unnamed seedling, derived from the varieties Elizabeth the Queen, Rose O'Day and Gloaming, and Innocence (all unpatented). The seedling was the seed parent and Innocence the pollen parent. Hand cross pollenization was done by me in my field at St. Charles, Minnesota, and no precaution was taken to prevent admixture by bees or insects.

This new variety has been asexually reproduced by me in Minnesota and California by natural increase from cormels through several generations and its characteristics have proven to be premanently fixed.

The illustration, made a part of this application, shows a single bloom spike, reduced in size, and is as nearly true to color as it is possible to depict. The illustration shows quite accurately the color, ruffling, recurved form, sharp blotch and spike formation.

In the following detailed description, color plate references are to "The Horticultural Colour Chart" by the British Colour Council. Where there are other references to color, the ordinary dictionary meanings of the terms are intended.

*The plant*

Growth: Extremely rugged grower, attaining a height of 58 to 60 inches over-all. Excellent propagator. Vigorous grower from cormlets.

Blooming: Blooms in about 70 days from large bulbs.

Stems: Slender stem; ⅜-inch in diameter. Stem is light pink above the bulb.

Foliage: Deep, blue-green; upright plant with outer leaves semi-drooping. Leaves are 1½ inches wide. Plant foliage, excluding the flower spike, is 36 inches high.

Disease resistance: Unusually rugged and free from disease.

Corms: Round, high-crowned; well husked. Flesh is straw color.

*The flower*

Spike: Flowerhead is 27 inches in length, with nineteen to twenty buds of which seven to eight open at one time.

Bud:
- *Size.*—Opening buds are 2½ inches across.
- *Opening.*—Five show color at one time.

Flower:
- *Arrangement.*—Florets are formal to semi-formally placed.
- *Size.*—Individual florets are 5 to 5½ inches in diameter.
- *Form.*—Round, ruffled and recurved.
- *Keeping qualities.*—Opens well on the plant but not from tight bud.

Petals:
- *Shape.*—Round; ruffled at edges.
- *Size.*—Upper petals 2¼ inches across; lip petals, 1½ inches.
- *Aspect.*—Extremely heavy substance.
- *Fragrance.*—None.
- *Color.*—Outer edges shade from $oo27/_1$ to $oo27/_2$ of Erythrite Red, thence, Geranium Lake $20/_2$ to $20/_3$ in the heart of the floret. Large blotch and mid-ribs are creamy white. Reverse of florets have more intense, broad areas of the deepest shades of both Erythrite Red and Geranium Lake.

Reproductive organs:
- *Stamens.*—Cream; purple pollen.
- *Pistil.*—Cream.

*Comparisons*

My new variety resembles Plum Pudding (unpatented), more than any other variety but differs from it principally as follows:

(1) It has sharper color contrast between floret and blotch.

(2) It is redder in color.

(3) It is not quite as formal in placement.

(4) It blooms much earlier.

Having thus disclosed my invention, I claim:

The new and distinct variety of gladiolus plant, substantially as herein shown and described, characterized by its unique blossom color, sharp, round, contrasting blotch, heavy substance, extreme ruffling and rugged vigor.

No references cited.

ABRAHAM G. STONE, *Primary Examiner.*
R. E. BAGWILL, *Assistant Examiner.*